United States Patent
Matthews et al.

(10) Patent No.: US 6,727,502 B1
(45) Date of Patent: Apr. 27, 2004

(54) CALIBRATION TECHNIQUE FOR COINCIDENCE IMAGING SYSTEMS

(75) Inventors: Christopher G. Matthews, Lyndhurst, OH (US); Wenli Wang, Aurora, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 210 days.

(21) Appl. No.: 09/893,934

(22) Filed: Jun. 27, 2001

(51) Int. Cl.[7] .............................................. G01T 1/164
(52) U.S. Cl. .............................. 250/363.03; 250/363.02
(58) Field of Search ........................ 250/363.03, 363.02, 250/363.01, 361, 336.1

(56) References Cited

U.S. PATENT DOCUMENTS

| | | | | |
|---|---|---|---|---|
| 5,793,045 A | * | 8/1998 | DiFilippo et al. | 250/363.03 |
| 5,900,636 A | * | 5/1999 | Nellemann et al. | 250/363.04 |
| 6,140,650 A | * | 10/2000 | Berlad | 250/363.09 |
| 6,294,788 B1 | * | 9/2001 | Cooke et al. | 250/363.03 |

* cited by examiner

Primary Examiner—David Porta
Assistant Examiner—Christine Sung
(74) Attorney, Agent, or Firm—Fay, Sharpe, Fagan, Minnich & Mckee, LLP

(57) ABSTRACT

An imaging method using a plurality of radiation detectors (12) is disclosed. A plurality of coincidence radiation events are measured (60) associated with a point radiation source (18). Initial values are assigned (62) for fitting parameters. Lines of response (LOR) are calculated (64) based upon the fitting parameters and the measured radiation events. A figure of merit is generated (66) that characterizes the apparent size of the point radiation source based upon the LOR's. The fitting parameters are optimized (70) using a minimization algorithm which includes iteratively repeating the calculating (64) and generating (66) steps to produce a minimized figure of merit. Correction factors are extracted from the optimized fitting parameters (72). A set of radiation data is acquired from an associated subject. The radiation data is corrected for mechanical camera misalignment by correcting the spatial coordinates of the detected radiation events using the correction factors. An image representation is reconstructed from the corrected radiation data.

20 Claims, 6 Drawing Sheets

CALIBRATION TECHNIQUE FOR COINCIDENCE IMAGING SYSTEMS

BACKGROUND OF THE INVENTION

The present invention relates to medical imaging systems. It finds particular application in the calibration of positron emission tomography (PET) or coincidence-capable gamma camera medical imaging systems, and will be described with particular reference thereto. It is to be appreciated that the invention may also find application in other types of nuclear cameras as well as other types of diagnostic imaging with two dimensional rotatable detectors.

A number of types of radiological events produce two emission photons which travel outward in exactly opposite directions. For example, a positron-electron annihilation event produces such an oppositely directed photon pair. Coincidence imaging systems take advantage of this geometric property in spatially localizing the radiological event to a line of response (LOR). The LOR is defined as the line connecting two simultaneous radiation detection events, which are presumed to correspond to detection of the two oppositely directed photons. Two detection events are typically judged to be simultaneous, or coincident, if both detections occur within a preselected coincidence time window. The radiological event, e.g. the positron-electron annihilation, will have occurred at some point along the LOR. Ideally, for an approximate point source which generates many positron-electron annihilation events within a very confined space, the LOR corresponding to each annihilation event will pass through the point source, and the point source may thus be located in two-dimensional or three-dimensional space, dependent upon the geometry of the detector system. Similarly, an extended radiological source, such as an organ which has absorbed an appropriate administered radiopharmeceutical, may be studied by reconstructing the LOR's corresponding to electron-positron annihilation events generated by the radiopharmeceutical into an image.

Non-idealities in real detection systems, such as mechanical misalignments, degrade image resolution. For example, misalignment of the radiation detectors blurs the image. The precision with which the radiation detectors can be mechanically aligned is limited by the weight and bulkiness of the shielded detectors, and the alignment precision required for adequate image resolution is often not practically attainable by purely mechanical procedures. Alignment-related resolution problems are particularly acute for positron coincidence imaging using a multi-head single photon emission computed tomography (SPECT) gamma camera with coincidence circuitry, often referred to as a gamma-PET imaging system. The gamma-PET provides a versatile and less expensive alternative to a dedicated PET imaging system, but the typically large heads and rotating gantry complicate mechanical alignment.

Improved resolution can be obtained by following the mechanical alignment with a calibration step. The calibration step preferably determines correction factors for the positional coordinates of each detector. The correction factors may subsequently be applied during data acquisition or analysis to improve image resolution. Gamma-PET systems have been calibrated using a SPECT data acquisition mode, the results of which are applied when operating the system in a PET or SPECT imaging mode. This approach corrects for the tangential detector head coordinate. However, SPECT is not strongly sensitive to the radial and orientational detector coordinate parameters. An additional disadvantage of calibration in SPECT mode is that subsequent to calibration the detector heads are re-positioned into the PET configuration, which may introduce additional misalignment not accounted for by the prior SPECT calibration.

The present invention contemplates a calibration procedure for coincidence imaging systems such as gamma-PET and dedicated PET systems, which overcomes the above shortcomings and others.

SUMMARY OF THE INVENTION

In accordance with one aspect of the present invention, a method for calibrating a coincidence imaging system which includes a plurality of radiation detectors is disclosed. A plurality of coincidence radiation events associated with a point radiation source are measured. Initial values are assigned for a set of fitting parameters. A minimization algorithm is applied, which includes calculating lines of response (LOR) based upon the fitting parameters and the measured radiation events, generating a figure of merit characterizing the apparent size of the point radiation source based upon the LOR's, and optimizing the fitting parameters to produce a minimized figure of merit. After the minimization, a correction factor relating to a positional coordinate of a detector is extracted from the fitting parameters.

In accordance with another aspect of the present invention, a method for imaging using a plurality of radiation detectors is disclosed. A plurality of coincidence radiation events associated with a point radiation source are measured. Initial values are assigned for at least one fitting parameter. Lines of response (LOR) are calculated based upon the at least one fitting parameter and the measured radiation events. A figure of merit is generated that characterizes the apparent size of the point radiation source based upon the LOR's. The at least one fitting parameter is optimized using a minimization algorithm which includes iteratively repeating the calculating and generating steps to produce a minimized figure of merit. At least one correction factor is extracted from the at least one optimized fitting parameter. A set of radiation data is acquired from an associated subject. The radiation data is corrected for camera misalignment by correcting the spatial coordinates of the detected radiation events using the at least one correction factor. An image representation is reconstructed from the corrected radiation data.

Preferably, the at least one fitting parameter includes a parameter related to the radial positional coordinate of a detector, a parameter related to the tangential positional coordinate of a detector, and a parameter related to the orientational positional coordinate of a detector. For a multiple-head imaging system, the fitting parameters preferably include: $\Delta r_i$, i=1 to N, where $\Delta r_i$ is a correction for the radial coordinate of the ith detector; $\Delta t_j$, j=1 to N, where $\Delta t_j$ is a correction for the tangential coordinate of the jth detector; and $\Delta \theta_k$, k=2 to N, where $\Delta \theta_k$ is a correction for the orientational coordinate of the kth detector.

The figure of merit is preferably generated by summing the distance or the square of the distance of closest approach of each LOR to a spatial point, in which case the positional coordinates of the spatial point are fitting parameters. Preferably, LOR's whose distance of closest approach is greater than a preselected distance are discarded. Alternatively, the figure of merit is generated by obtaining the crossing point or the distance of closest approach of each pair of LOR's and calculating the standard deviation of the crossing points or the obtained distances.

In accordance with yet another aspect of the present invention, a method of PET imaging is disclosed. Coincidence radiation events from a calibration source are detected with at least two detector heads. Correction factors that correct for mechanical misalignment of the detector heads are calculated from the coincidence detected calibration source radiation. During a diagnostic imaging procedure performed on a subject, image data are generated in response to radiation collected with the detector heads. The image data are corrected with the correction factors. The corrected image data are reconstructed into an image representation.

In accordance with still yet another aspect of the present invention, a coincidence imaging system is disclosed. The system includes a gantry. A plurality of flat panel detectors are disposed about the gantry. A data memory stores measured data about radiation events detected by the detectors. A calibration memory stores a plurality of calibration parameters for correcting data measured during a patient scan. A processor in communication with the calibration memory and with the data memory calculates the calibration parameters by a minimization algorithm that includes optimizing fitting parameters with respect to acquired radiation data associated with a point radiation source.

Preferably, the calibration parameters include parameters relating to positional coordinates of the plurality of detectors. The gantry is preferably rotatable. The figure of merit is preferably generated by summing the square of the distance of closest approach of each LOR to a spatial point, in which case the positional coordinates of the spatial point are fitting parameters. Alternatively, the figure of merit is generated by obtaining the crossing point of each pair of LOR's and calculating the variance of the crossing points. To reduce noise, the minimization algorithm preferably discards measured data about radiation events whose energy is outside a preselected energy range.

One advantage of the present invention is that the calibration is performed in coincidence imaging mode and does not require mechanical re-configuration the system between calibration and PET imaging.

Another advantage of the present invention is that it simultaneously calibrates all three detector head positional coordinates, e.g. the radial, tangential, and orientational coordinates.

Another advantage of the present invention is that it provides improved image quality.

Yet another advantage of the present invention is that it is compatible with both gamma-PET and dedicated PET systems.

Still further advantages and benefits of the present invention will become apparent to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for the purposes of illustrating preferred embodiments and are not to be construed as limiting the invention.

DETAILED DESCRIPTION OF THE PREFERRED EMBODIMENTS

The invention will be described with reference to a three-head gamma-PET system. However, it is to be appreciated that the invention is not so limited, and may instead be applied to other coincidence imaging systems such as dedicated PET systems, systems with two or more heads, and other systems that reconstruct images based on a line of response.

Figure 1:
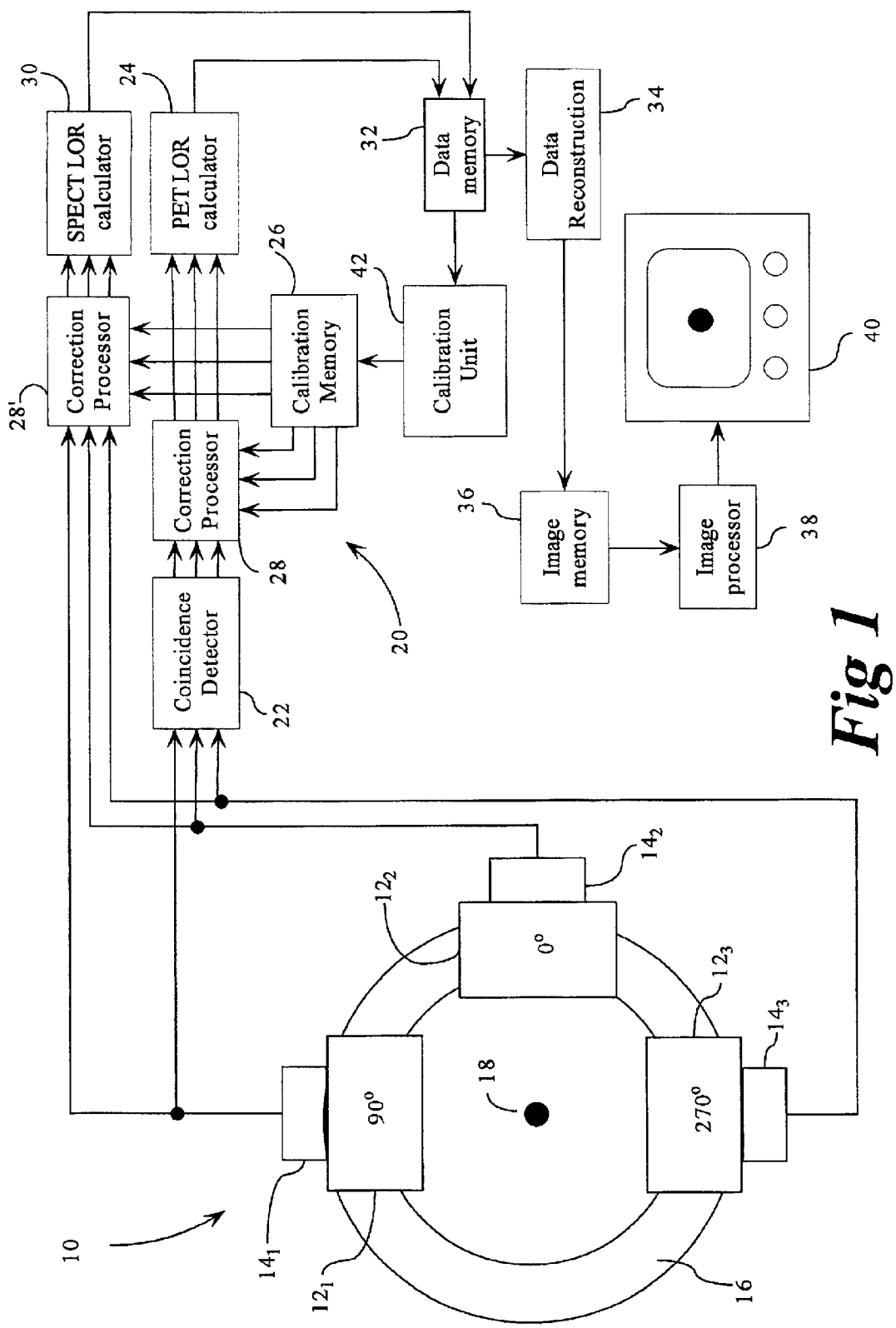
FIG. 1 shows a diagrammatic representation of a gamma-PET system.

With reference to FIG. 1, a detector system 10 includes detector heads 12, in the instant gamma-pet system three heads denoted $12_1$, $12_2$, and $12_3$. Each head includes a detector processor unit $14_1$, $14_2$, $14_3$ which identifies the coordinates of a radiation detection event on the detector face. As shown in FIG. 1, the detectors are mounted on a gantry 16 at 0°, 90°, and 270° orientations. However, other numbers and orientations of heads can be used. The specified orientations are to be taken as approximate values only, because as noted above mechanical alignment is not precise. It is also pointed out that the gamma-PET system is a versatile medical imaging system which also includes SPECT capability. The gantry 16 is preferably rotatable. For nuclear medicine imaging, a subject (not shown) is positioned in the receiving area located within gantry 16. For calibration, a point source 18 is positioned in the receiving area, as shown. Of course, for medical diagnostic imaging the point source is replaced by an associated patient.

With continuing reference to FIG. 1, radiation detection events detected by detector system 10 are collected by a LOR calculating circuit 20. The LOR calculator 20 includes a coincidence detector 22 that determines when two events are within a preselected temporal window of being simultaneous. When two events are determined to be coincident, the identification of the detector heads, the coordinates of the radiation detection point on each detecting head, and the angular orientation of the gantry are supplied to a PET LOR calculator 24 that calculates a ray or line between the two radiation detection points. The spatial coordinates of the radiation detection events in the heads are corrected by correction factors retrieved from a correction memory 26. For example, the retrieved correction factors are offsets that a correction processor 28 uses to adjust the apparent spatial locations of the radiation events in the heads prior to the line of response (LOR) calculation. Alternatively, the line of response can be calculated first and then corrected with the correction factors.

In SPECT imaging, the identification of the detecting head, the coordinates on the detecting head, the angular orientation of the gantry and heads, and identification of the collimator characteristics of the head collimator are communicated to a SPECT line of response calculator 30 that calculates a trajectory or line traversed by the received radiation. Correction factors from the calibration memory 26 are again retrieved and used by a correction processor 28' to correct the SPECT trajectory or LOR.

The acquired and corrected LOR data are preferably stored in a data memory or buffer 32. A data reconstruction processor 34 reconstructs an electronic image representation from the LOR data stored in data memory 32 and stores the resultant image representation in an image memory 36. Portions of the stored image representation are retrieved by an image processor 38 and converted to an appropriate format for display on a monitor 40, such as a video, CCD, active matrix, or other monitor. Of course, a color printer or other output device may also be used to present the data in a convenient format.

To generate the contents of calibration memory 26, a point radiation source 18 is disposed in view of the detectors $12_1$, $12_2$, $12_3$. Of course, the point radiation source 18 has physical size, which is however preferably smaller than the desired calibrated image resolution. LOR data is measured for the point source 18. The calibration memory 26 contents are not applied during this data acquisition so that data without any calibration are stored in the data memory 32. Alternatively, if calibration data from a previous calibration is presently stored in calibration memory 26, this calibration may be applied as an initial condition (not shown). A calibration unit 42 calculates new calibration data from the measurement of the point source 18, and the new calibration data is stored in the calibration memory 26 for use in future imaging as described above.

The method by which the calibration processor 42 calculates new calibration data is based upon the recognition that the LOR's should all intersect at the coordinates of the point source 18. When they fail to intersect, the calibration processor mathematically varies the coordinates of the detector heads until the separation of the rays is minimized at a point corresponding to the position of the point source 18. It will be particularly noticed that the calibration is done in PET mode, with the detector system 10 in the PET configuration identical to that used for PET measurements. Thus, PET imaging can commence immediately after calibration and replacement of the point radiation source 18 by a subject, e.g. a patient, with no adjustments being made to the detector system 10. This approach advantageously avoids the potential for introducing new detector misalignments during the detector system 10 reconfiguring.

Figure 2A:
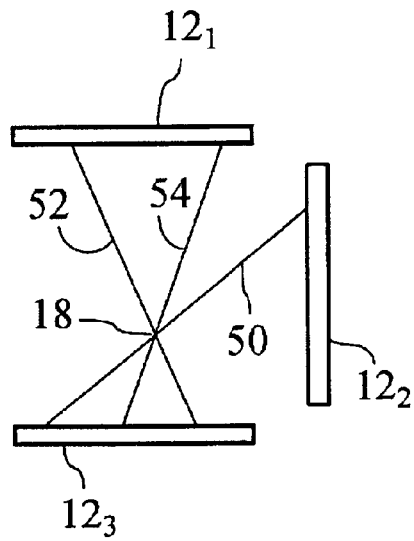
FIG. 2A shows a diagrammatic representation of a measurement of a point source using a well-aligned three-head PET system.

With reference to FIGS. 2A to 2D, typical contents for configuration memory 26 will be described. FIG. 2A shows an ideal, perfectly aligned three-head gamma-PET system measuring an ideal point radiation source 18. Three representative lines of response (LOR) 50, 52, 54 are shown, corresponding to three positron-electron annihilation events in the point radiation source 18. The LOR 50 is detected by detectors $12_2$ and $12_3$; the LOR's 52 and 54 are detected by detectors $12_1$ and $12_3$. Of course, the three event pairs represented by LOR's 50, 52, and 54 are temporally separated so that the detection system 10 is able to distinguish the events. Because LOR's 50, 52, and 54 originate from the point radiation source 18, in a perfectly aligned system the three LOR's intersect at a point corresponding exactly to the spatial location of the point radiation source 18.

Figure 2B:
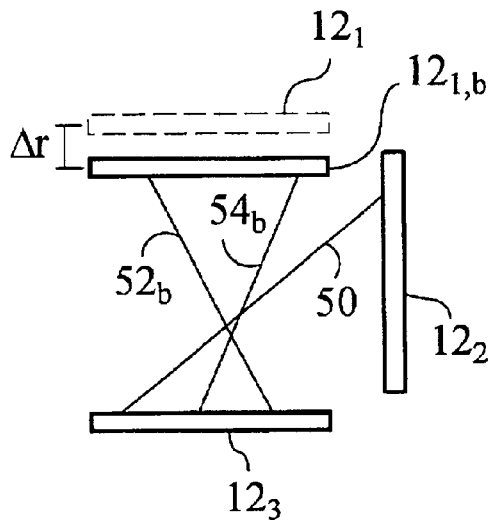
FIG. 2B shows a diagrammatic representation of a measurement of a point source using a three-head PET system in which one head has a radial misalignment $\Delta r$.

With reference to FIG. 2B, the case where detector $12_1$ is misaligned by a radial error $\Delta r$ is presented. In FIG. 2B, the dashed box $12_1$ is the actual position of detector, while box $12_{1,b}$ is the position of the detector erroneously reported to the data acquisition unit 20. Because of the radial misalignment $\Delta r$, the LOR's 52, 54 of FIG. 2A which involved detection events on detector $12_1$ are now incorrectly calculated in FIG. 2B as $52_b$ and $54_b$ respectively. The three LOR's 50, $52_b$, and $54_b$ do not intersect at a single point. If the detector system with the radial misalignment of FIG. 2B is used for gamma-PET imaging without calibration, the resultant image will be degraded due to the misalignment $\Delta r$.

Figure 2C:
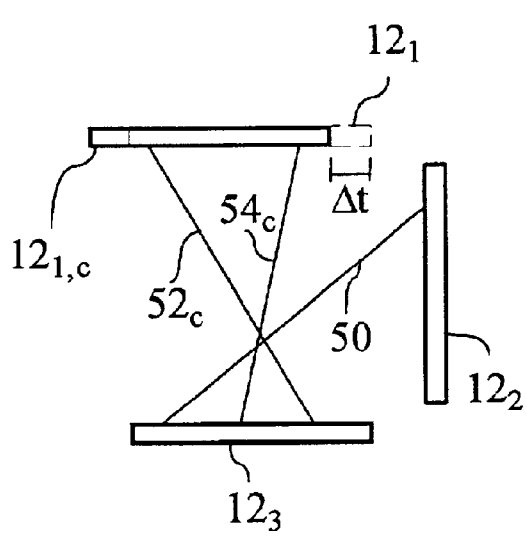
FIG. 2C shows a diagrammatic representation of a measurement of a point source using a three-head PET system in which one head has a tangential misalignment $\Delta t$.
Figure 2D:
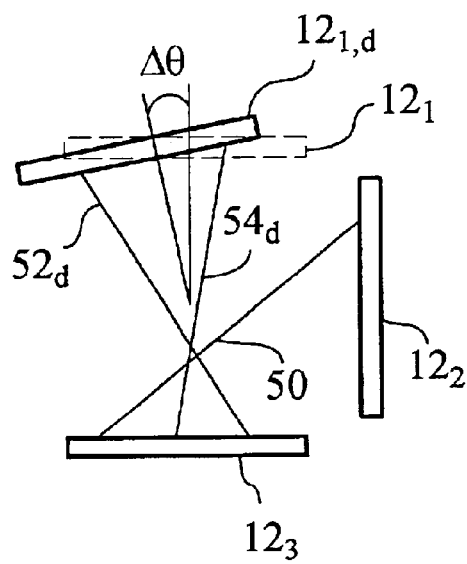
FIG. 2D shows a diagrammatic representation of a measurement of a point source using a three-head PET system in which one head has a orientational misalignment $\Delta \theta$.

FIG. 2C shows the effect of a tangential misalignment $\Delta t$. Again, ideal LOR's 52, 54 of FIG. 2A are incorrectly calculated as $52_c$ and $54_c$ respectively, resulting in image blurring. FIG. 2D shows the effect of an orientational misalignment $\Delta \theta$, which produces incorrect LOR's $52_d$ and $54_d$ which again result in image degradation. Of course, it is to be recognized that misalignments of two or even three positional coordinates may occur simultaneously in a given detector head, and that any or all detector heads may be misaligned. Preferably, calibration memory 26 includes corrections at least for radial misalignment $\Delta r$, tangential misalignment $\Delta t$, and orientational misalignment $\Delta \theta$ of each detector head $12_1$, $12_2$, $12_3$.

Figure 3:
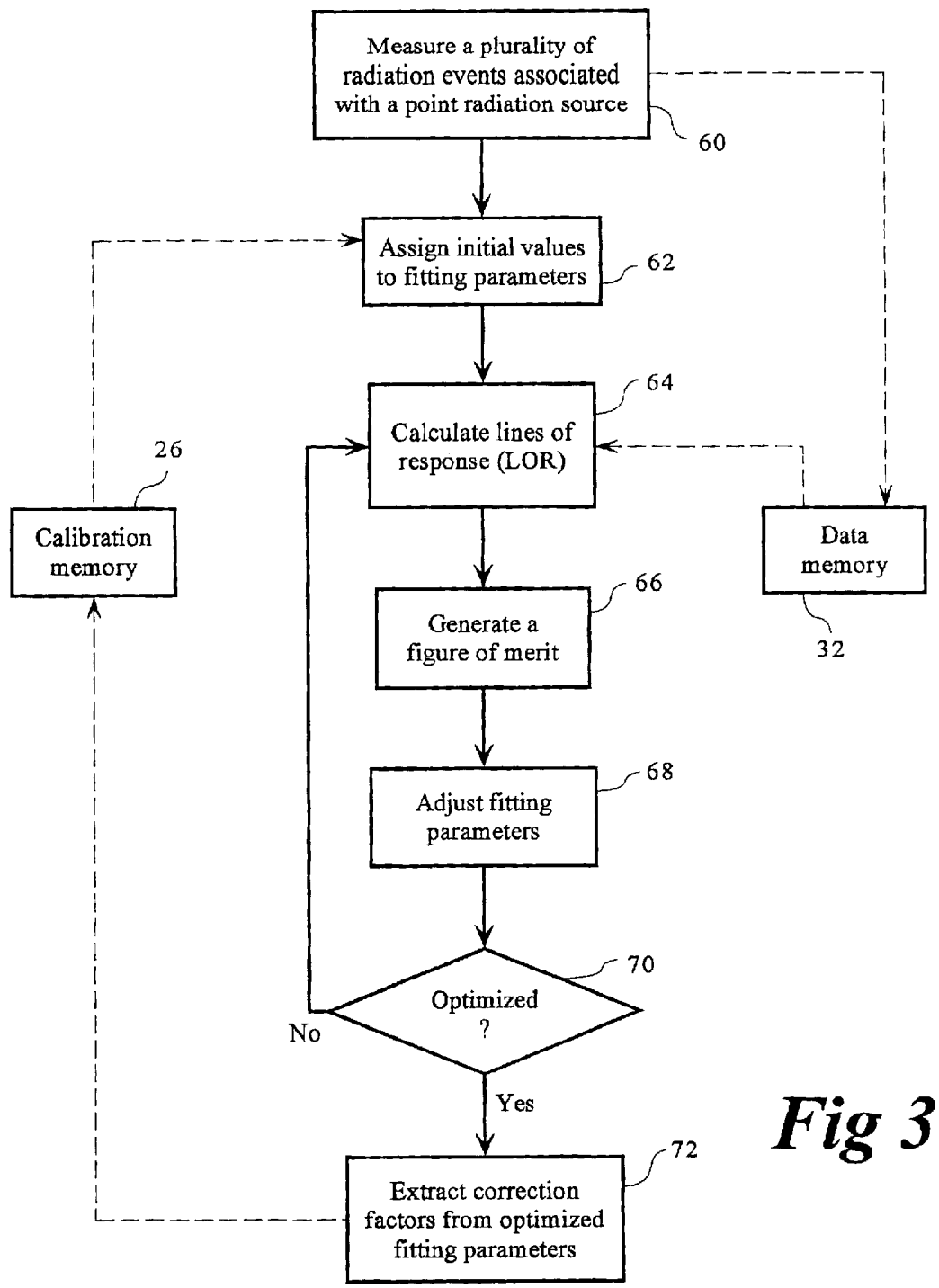
FIG. 3 is a flowchart of a preferred embodiment of the calibration method.
Figure 4:
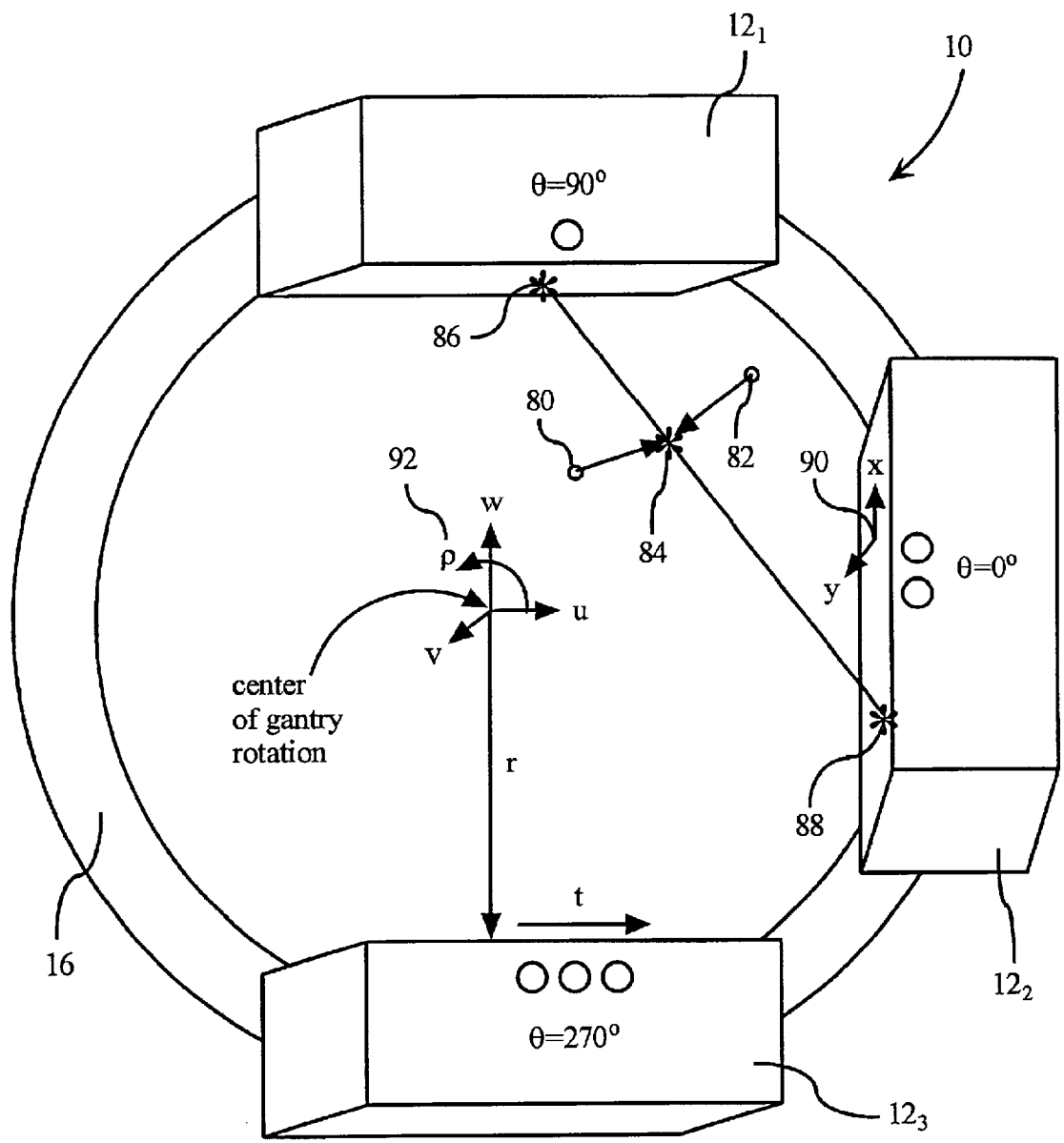
FIG. 4 shows two radiation detection events corresponding to a single electron-positron annihilation event, along with the spatial coordinate systems used in tabulating and analyzing detection data.

With reference to FIGS. 1, 3, and 4 a preferred method performed by the calibration processor 42 for calibrating a coincidence imaging system which includes a plurality of radiation detectors is disclosed. As shown in FIG. 1, the point radiation source 18 is positioned in the receiving area of the detector system 10 which is configured in the PET imaging mode. The system measures 60 a plurality of radiation events associated with the point radiation source 18. The calibration method uses a minimization method to optimize parameters of interest. More specifically, initial values are assigned 62 to the fitting parameters. The fitted parameters are preferably: $\Delta r_i$, i=1 to 3, where $\Delta r_i$ is a correction for the radial coordinate of the ith detector; $\Delta t_j$, j=1 to 3, where $\Delta t_j$ is a correction for the tangential coordinate of the jth detector; and $\Delta \theta_k$, k=2 to 3, where $\Delta \theta_k$ is a correction for the orientational coordinate of the kth detector. It will be noticed that there is no correction for the orientational coordinate of the k=1 detector. This is because one detector defines the reference orientation. With this reduction, there are 8 fitting parameters corresponding to the detector positional coordinate corrections. In the step 62, initial values for these positional coordinate correction parameters is typically set to zero. Alternatively, if the calibration memory 26 contains values from a previous calibration it may be preferable to use these prior values to initialize the corresponding fitting parameters.

The iterative minimization loop begins by calculating the lines of response (LOR's) 64. With reference to FIG. 4 which shows the detector system 10 in simplified form, an electron 80 and positron 82 annihilate at a spatial point 84 and the annihilation emits two oppositely directed photons. One photon is detected at a spot 86 on the detector $12_1$, while the other photon is detected at a spot 88 on the detector $12_2$. Detection events 86 and 88 are recognized as simultaneous events because the time separation between the two detection events is less than a preselected coincidence time window. Preferably, the detections are recorded in a format such as $(h_1, x_1, y_1, e_1, h_2, x_2, y_2 e_2, \rho)$, where $h_i$ identifies the head, $(x_i, y_i)$ identify the detection spot on the face of detector $h_i$ using the (x, y) coordinate system 90, $e_i$ is the photon energy, and $\rho$ is the gantry rotation angle 92. The LOR is defined with respect to a detector-independent coordinate system, preferably with respect to the gantry coordinate system (u, v, w). The position of each head in the gantry coordinate system is calculable from the radial coordinate r, tangential coordinate t, and the orientational coordinate θ. In FIG. 4, the head $12_1$ has θ=90° and head $12_2$ has θ=0°. The LOR is then defined by its endpoints which are the detection points 86, 88 given in gantry coordinate system (u, v, w) as:

$$u_j = (x_j + t_{h_j}(\rho))\cos(\theta_{h_j}+\rho) + r_{h_j}(\rho)\sin(\theta_{h_j}+\rho)$$

$$v_j = y_j$$

$$w_j = (x_j + t_{h_j}(\rho))\sin(\theta_{h_j}+\rho) - r_{h_j}(\rho)\cos(\theta_{h_j}+\rho) \quad (1)$$

where j=1,2 corresponding to the two detector heads. It will be noticed that in equation (1) tangent t and radius r are written as functions or gantry rotation ρ, thereby accounting for a non-circular orbit. For a circular orbit, tangent t and radius r are independent of gantry rotation ρ. The LOR is thus defined by the detection point coordinates $(u_1, v_1, w_1)$ and $(u_2, v_2, w_2)$. In performing the LOR calculations, the correction parameter values of the present iteration are used. That is, the position of each radiation detector is corrected by the present iteration correction values for the radial, tangential, orientational coordinates of the detector when applying equation (1).

In the iterative minimization method, a figure of merit is minimized. The figure of merit is selected to provide a measure of how closely the LOR's come to passing through a single point in space corresponding to the point radiation source 18. Alternatively, the closest approach of the LOR's to one another defines a presumed source region, and the figure of merit would then preferably define the size of this source region, which as the minimization reduces the figure of merit would effectively reduce the source region toward a point. Two figures of merit are presently preferred, although other figures of merit are also possible and fall within the scope of the invention.

Figure 5:
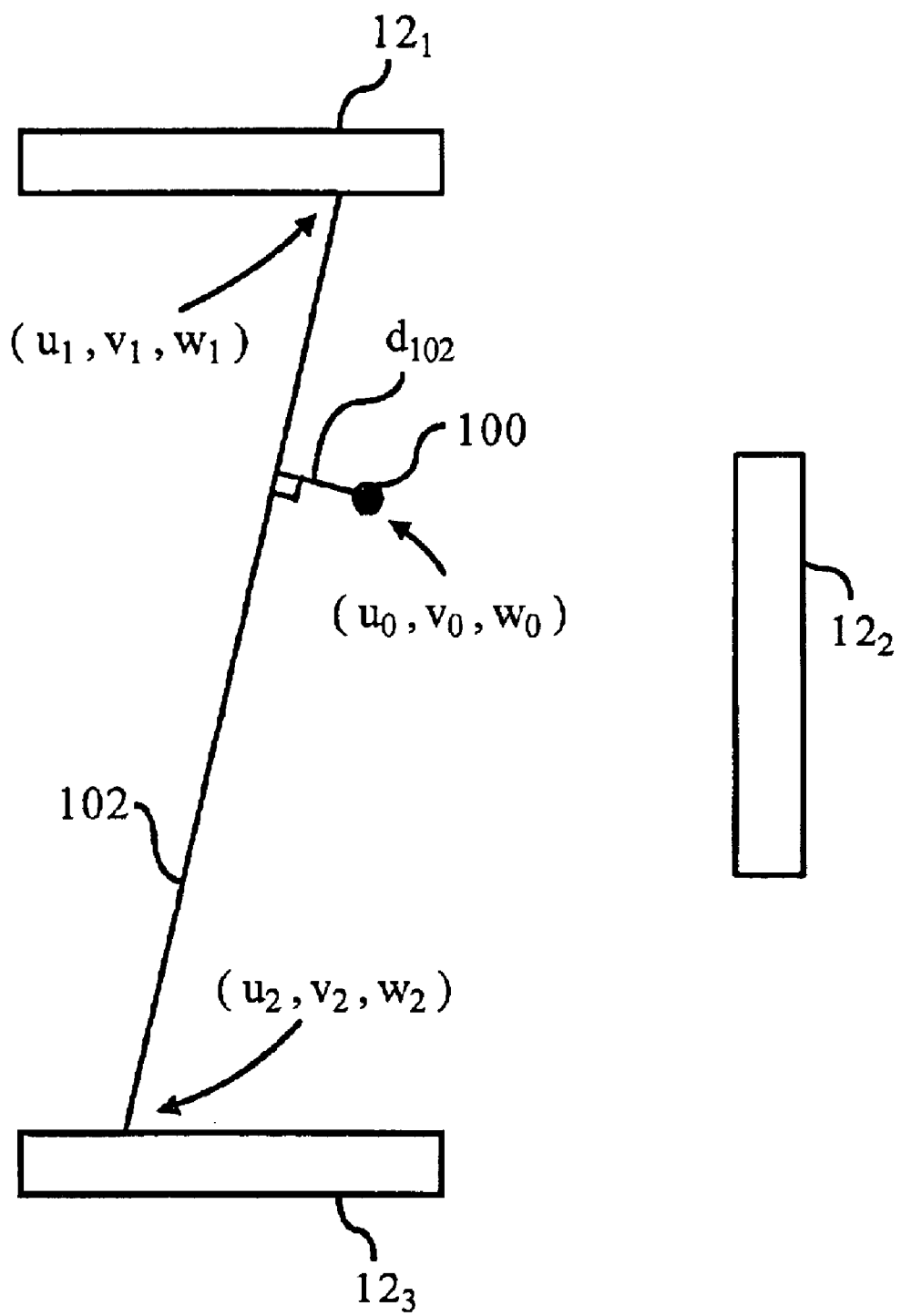
FIG. 5 is a diagrammatic illustration of the calculation of a preferred figure of merit.

With reference to FIG. 5, a first preferred figure of merit is described. A spatial point 100 is defined in space by its gantry coordinates $(u_0, v_0, w_0)$, and the figure of merit is calculated by summing the distance between the point 100 and the closest approach of each LOR. For example, in FIG. 5 a LOR 102 detected by a detection point $(u_1, v_1, w_1)$ on the detector $12_1$, and by a detection point $(u_2, v_2, w_2)$ on the detector $12_3$, has a closest approach $d_{102}$ as indicated on FIG. 5. Alternatively, instead of summing the distances, the sum may be over the square of the distance, providing a conventional least-squares minimization approach. Given the two endpoints of a LOR: $(u_1, v_1, w_1)$, $(u_2, v_2, w_2)$ and the coordinates of the spatial point $(u_0, v_0, w_0)$, the point-to-LOR distance d may be calculated as:

$$d^2 = \frac{\begin{vmatrix} v_0 - v_1 & w_0 - w_1 \\ v_2 - v_1 & w_2 - w_1 \end{vmatrix}^2 + \begin{vmatrix} w_0 - w_1 & u_0 - u_1 \\ w_2 - w_1 & u_2 - u_1 \end{vmatrix}^2 + \begin{vmatrix} u_0 - u_1 & v_0 - v_1 \\ u_2 - u_1 & v_2 - v_1 \end{vmatrix}^2}{(u_2 - u_1)^2 + (v_2 - v_1)^2 + (w_2 - w_1)^2} \quad (2)$$

where the (u, v, w) coordinates are all in the gantry coordinate system.

Whether the figure of merit is summed over d or $d^2$, the coordinates of the spatial point $(u_0, v_0, w_0)$ are preferably included as fitting parameters in addition to the eight detector positional correction parameters specified earlier, giving an eleven parameter fit when using this figure of merit. However, since the gantry coordinates of the approximate point radiation source are initially known to within the mechanical alignment precision, the initial values for coordinates $(u_0, v_0, w_0)$ are typically close to the final fitted values.

Figure 6:
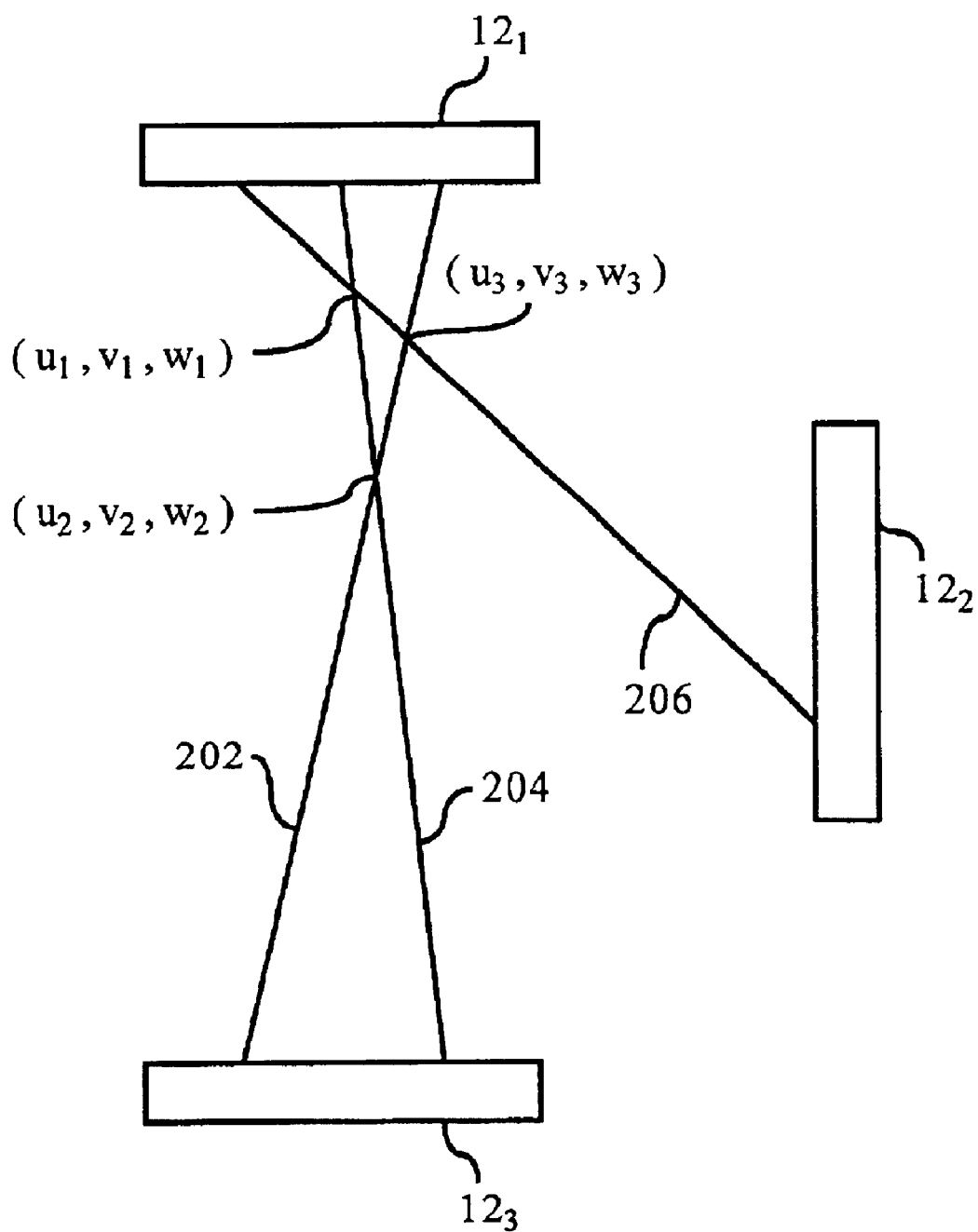
FIG. 6 is a diagrammatic illustration of the calculation of another preferred figure of merit.

With reference to FIG. 6, a second preferred figure of merit characterizes the crossing point (in two dimensions) or the distance of closest approach (in three dimensions) between each pair of LOR's. In the exemplary FIG. 6, three LOR's 202, 204, 206 cross in two dimensions at spatial points with coordinates $(u_1, v_1, w_1)$, $(u_2, v_2, w_2)$, and $(u_3, v_3, w_3)$. The figure of merit is then the variance or standard deviation of the resultant crossing point distribution or distance distribution. This figure of merit does not require the additional three fitting parameters corresponding to the coordinates of a mathematical spatial point. However, because the relation between every pair of LOR's is calculated, this figure of merit is more computationally involved compared with the first figure of merit.

With the fitting parameters defined and initialized and a figure of merit selected, any standard minimization technique may be employed to adjust the fitting parameters 68 and conditionally iterate until optimization is achieved 70. The preferred optimization method is Powell's method, but other methods such as the Marquardt least squares optimization algorithm may also be employed. When a minimum is reached, the relevant correction factors such as radial corrections $\Delta r_i$, tangential corrections $\Delta t_j$, and orientational corrections $\Delta \theta_k$ are extracted 72 and stored in the calibration memory 26.

During the calibration process, several additional error-reduction methods are optionally employed. A low activity point radiation source is used to minimize the rate of "randoms", which are erroneously identified LOR's resulting from random simultaneous detection of two different radiation events. That is, two detection events occur with time separation less than the coincidence time window, but the photons did not in fact originate from a single positron-electron annihilation event. By using a low activity source, the likelihood of random simultaneous detection events is reduced. Additionally, using the smallest coincidence time window possible further reduces the rate of random LOR detections. Noise is further reduced by only accepting LOR's which fall within a window around the positron-electron annihilation energy. Preferably, a window of approximately 30% around the 511 keV positron-electron annihilation energy peak is used.

Finally, if the location of the point source is known or can be estimated, LOR's with a closest approach greater than a preselected threshold are discarded as being likely randoms or other noise events. A threshold distance of 10 mm is preferred. In the case of the first figure of merit wherein the distance or distance squared between the LOR and a spatial point is calculated, the threshold is preferably reduced during minimization process as the estimated location of the point source becomes more and more precise.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for calibrating a coincidence imaging system which includes a plurality of radiation detectors, the method comprising:

measuring a plurality of coincidence radiation events associated with a point radiation source;

assigning initial values for a set of fitting parameters;

applying a minimization algorithm including:

calculating lines of response (LOR) based upon the fitting parameters and the measured radiation events, generating a figure of merit characterizing the apparent size of the point radiation source based upon the LOR's, and optimizing the fitting parameters to produce a minimized figure of merit; and extracting from the optimized fitting parameters a correction factor relating to a positional coordinate of a detector.

2. A method for imaging using a plurality of radiation detectors, the method comprising:

measuring a plurality of coincidence radiation events associated with a point radiation source;

assigning initial values for at least one fitting parameter;

calculating lines of response (LOR) based upon the at least one fitting parameter and the measured radiation events;

generating a figure or merit characterizing the apparent size of the point radiation source based upon the LOR's;

optimizing the at least one fitting parameter using a minimization algorithm which includes iteratively repeating the calculating and generating steps to produce a minimized figure of merit;

extracting from the at least one optimized fitting parameter at least one correction factor;

acquiring a set of radiation data from an associated subject;

correcting the radiation data for camera misalignment by correcting the spatial coordinates of the detected radiation events using the at least one correction factor; and reconstructing an image representation from the corrected radiation data.

3. The imaging method as described in claim 2, wherein the at least one fitting parameter includes:

a parameter related to the radial positional coordinate of a detector.

4. The imaging method as described in claim 2, wherein the at least one fitting parameter includes:

a parameter related to the tangential positional coordinate of a detector.

5. The imaging method as described in claim 2, wherein the at least one fitting parameter includes:

a parameter related to the orientational positional coordinate of a detector.

6. The imaging method as described in claim 2, wherein:

the step of generating a figure of merit includes summing a distance of closest approach of each LOR to a spatial point; and the at least one fitting parameter includes the positional coordinates or the spatial point.

7. The imaging method as described in claim 2, wherein:

the step of generating a figure of merit includes summing the square of a distance of closest approach or each LOR to a spatial point; and the at least one fitting parameter includes the positional coordinates of the spatial point.

8. The imaging method as described in claim 7, wherein the step of generating a figure of merit further includes:

discarding LOR's whose distance of closest approach is greater than a preselected distance.

9. The imaging method as described in claim 2, wherein the step of generating a figure of merit further includes:

obtaining a crossing point of each pair of LOR's; and calculating a standard deviation of the crossing points.

10. The imaging method as described in claim 2, wherein the step of generating a figure of merit further includes:

obtaining a distance of closest approach for each pair of LOR's; and calculating a standard deviation of the obtained distances.

11. The imaging method as described in claim 2, wherein the number of detectors is N and the fitting parameters include:

$\Delta r_i$, i=1 to N, where $\Delta r_i$ is a correction for the radial coordinate of the ith detector;

$\Delta t_j$, j=1 to N, where $\Delta t_j$ is a correction for the tangential coordinate of the jth detector; and $\Delta \theta_k$, k=2 to N, where $\Delta \theta_k$ is a correction for the orientational coordinate of the kth detector.

12. The imaging method as described in claim 11, wherein the fitting parameters further include:

positional coordinates of the point radiation source.

13. A method of PET imaging comprising:

coincidence detecting radiation events from a calibration source with at least two detector heads;

calculating correction factors that correct for mechanical misalignment of the detector heads from the coincidence detected calibration source radiation, the calculating including:

generating a figure of merit which characterizes an apparent size of a point source of radiation based on lines of response, optimizing fitting parameters based on the figure of merit;

during a diagnostic imaging procedure performed on a subject, generating image data in response to radiation collected with the detector heads;

correcting the image data with the correction factors; and reconstructing the corrected image data into an image representation.

14. A coincidence imaging system comprising:

a gantry;

a plurality of flat panel detectors disposed about the gantry;

a data memory which stores measured data about radiation events detected by the detectors;

a calibration memory which stores a plurality of calibration parameters for correcting data measured during a patient scan; and a processor in communication with the calibration memory and with the data memory which calculates the calibration parameters by a minimization algorithm that includes:

generating a figure of merit characterizing an apparent size of a measured point radiation source, and optimizing calibration parameters with respect to the figure of merit to minimize an apparent size of the point radiation source.

15. The imaging system of claim 14, wherein the minimization algorithm further includes:

discarding measured data about radiation events whose energy is outside a preselected energy range.

16. A coincidence imaging system comprising:

a gantry;

a plurality of detectors disposed about the gantry;

a data memory which stores measured data about radiation events detected by the detectors;

a calibration memory which stores a plurality of calibration parameters for correcting data measured during a patient scan; and a processor in communication with the calibration memory and with the data memory which calculates the calibration parameters which are extracted from fitting parameters using a minimization algorithm, the minimization algorithm including:

calculating lines of response (LOR) based upon the fitting parameters and the measured data;

generating a figure of merit characterizing the apparent size of the point radiation source based upon the LOR's; and optimizing the fitting parameters to produce a minimized figure of merit.

17. The imaging system of claim 16 wherein the calibration parameters include:

parameters relating to positional coordinates of the plurality of detectors.

18. The imaging system of claim 17, wherein:

the gantry is a rotatable gantry which acquires measured data over a range of gantry angular positions.

19. The imaging system of claim 16, wherein:

the figure of merit is generated by summing the square of a distance of closest approach of each LOR to a spatial point; and the fitting parameters include the positional coordinates of the spatial point.

20. The imaging system of claim 16, wherein the generating of the figure of merit includes:

obtaining a crossing point of each pair of LOR's; and calculating a variance of the crossing points.

* * * * *